(12) United States Patent
Nose et al.

(10) Patent No.: US 8,772,554 B2
(45) Date of Patent: Jul. 8, 2014

(54) PROCESS FOR PREPARING 2,3,3,3-TETRAFLUOROPROPENE

(75) Inventors: Masatoshi Nose, Settsu (JP); Yuzo Komatsu, Settsu (JP)

(73) Assignee: Daikin Industries, Ltd., Osaka (JP)

( * ) Notice: Subject to any disclaimer, the term of this patent is extended or adjusted under 35 U.S.C. 154(b) by 0 days.

(21) Appl. No.: 14/127,258

(22) PCT Filed: Jun. 22, 2012

(86) PCT No.: PCT/JP2012/066633
§ 371 (c)(1),
(2), (4) Date: Dec. 18, 2013

(87) PCT Pub. No.: WO2013/015068
PCT Pub. Date: Jan. 31, 2013

(65) Prior Publication Data
US 2014/0121424 A1    May 1, 2014

Related U.S. Application Data

(60) Provisional application No. 61/511,663, filed on Jul. 26, 2011.

(51) Int. Cl.
*C07C 17/20* (2006.01)
*C07C 21/18* (2006.01)

(52) U.S. Cl.
CPC .............. *C07C 17/206* (2013.01); *C07C 21/18* (2013.01)
USPC ....................................... 570/169; 570/165

(58) Field of Classification Search
CPC .............................. C07C 17/206; C07C 21/18
USPC ................................. 570/169, 165
See application file for complete search history.

(56) References Cited

U.S. PATENT DOCUMENTS

2009/0240090 A1    9/2009  Merkel et al.

FOREIGN PATENT DOCUMENTS

| WO | 2007/079431 | 7/2007 |
|----|-------------|--------|
| WO | 2008/054781 | 5/2008 |
| WO | 2009/158321 | 12/2009 |
| WO | 2010/101198 | 9/2010 |
| WO | 2010/123154 | 10/2010 |

OTHER PUBLICATIONS

International Search Report issued Septemeber 14, 2012 in International (PCT) Application No. PCT/JP2012/066633.
Written Opinion of the International Searching Authority issued Sep. 14, 2012 in International (PCT) Application No. PCT/JP2012/066633.

*Primary Examiner* — Elvis O Price
(74) *Attorney, Agent, or Firm* — Wenderoth, Lind & Ponack, L.L.P.

(57) ABSTRACT

The present invention provides a method for efficiently preparing 2,3,3,3-tetrafluoropropene (HFO-1234yf) by a simple and economically advantageous method that is suitable for implementation on an industrial scale. The present invention provides a process for preparing 2,3,3,3-tetrafluoropropene, comprising the step of: (1) in a reactor, (1-1) reacting 1,1,1,2,3-penta-chloropropane with hydrogen fluoride in an amount of 10 to 100 mol per mole of the 1,1,1,2,3-pentachloropropane 1; (1-2) in the presence of chromic oxide represented by composition formula: $CrO_m$ ($1.5<m<3$) or fluorinated chromic oxide obtained by fluorinating the chromic oxide; (1-3) in the presence of oxygen in an amount of 0.02 to 1 mol per mole of the 1,1,1,2,3-pentachloropropane; and (1-4) in the gas phase within a temperature range of 320 to 390 degrees centigrade, thereby obtaining a reaction product containing 2,3,3,3-tetrafluoropropene.

15 Claims, No Drawings though drawing attention as a component of refrigerants, mixed refrigerants, and the like that can be used as an alternative for chlorofluorocarbon. Additionally, 2,3,3,3-tetrafluoropropene is useful not only as a propellant, heat transfer medium, or fire-extinguishing agent, but also as a monomer component in a polymer.

PROCESS FOR PREPARING 2,3,3,3-TETRAFLUOROPROPENE

This is a National Stage of International Application No. PCT/JP2012/066633, filed Jun. 22, 2012, which claims priority to U.S. Provisional Application No. 61/511,663, filed Jul. 26, 2011, now abandoned.

TECHNICAL FIELD

The present invention relates to a process for preparing 2,3,3,3-tetrafluoropropene.

BACKGROUND ART 2,3,3,3-Tetrafluoropropene, which is a halopropene and represented by the chemical formula: $CF_3CF=CH_2$ (HFO-1234yf), is a useful compound as a refrigerant. 2,3,3,3-Tetrafluoropropene has zero ozone depletion potential (ODP) and an extremely low global warming potential (GWP), and is thus drawing attention as a component of refrigerants, mixed refrigerants, and the like that can be used as an alternative for chlorofluorocarbon. Additionally, 2,3,3,3-tetrafluoropropene is useful not only as a propellant, heat transfer medium, or fire-extinguishing agent, but also as a monomer component in a polymer.

As a preparation process for preparing HFO-1234yf, for example, Patent Literature 1 discloses a preparation method in which a compound represented by $CX_3CHClCH_2X$ (X is any halogen selected from F, Cl, Br, and I, and each X may be the same or different) is reacted with a Cr catalyst in the gas phase, thereby directly producing HFO-1234yf as a component of a product containing $CF_3CF=CH_2$ (HFO-1234yf). However, this method is not practical because its yield is low due to the formation of many impurities, and improvements are thus needed, and also because the catalyst is deteriorated in a short period of time.

Further, Patent Literature 2 listed below discloses a method for preparing HFO-1234yf in which HCC-1230xa represented by $CH_2ClCCl=CCl_2$ as a starting material is reacted with HF in the presence of a fluorinated catalyst so as to prepare HCFC-1233xf represented by $CF_3CCl=CH_2$, and further, HFO-1234yf is prepared via HCFC-244bb represented by $CF_3CFClCH_3$. However, this method has economic problems because the steps are complicated and long with many stages.

Additionally, Patent Literature 3 listed below discloses a method in which HCC-240db represented by $CCl_3CHClCH_2Cl$ as a starting material is reacted with HF in the gas phase at a reaction temperature of 255° C. in the presence of a fluorinated Cr catalyst. However, this method is not considered to be a practical preparation method of HFO-1234yf because HFO-1234yf is produced only in an amount of 0.5% in combination with HFC-245cb, and the main product is HCFC-1233xf (98.3% production).

Further, Patent Literature 4 listed below discloses a method for preparing HFO-1234yf in which HCC-1230xa represented by $CH_2ClCCl=CCl_2$ as a starting material is reacted with HF in the gas phase with oxygen entrainment in the presence of a fluorinated catalyst activated by HF at a pressure of 150 psi or higher, thereby preparing HFO-1234yf by a single-step reaction. However, because HCC-1230xa is used as a starting material in this method, catalyst deterioration due to olefin polymerization advances, and both oxygen entrainment and a stabilizer, such as a polymerization inhibitor, are required in order to inhibit the deterioration. This causes an increase in the economic cost.

As described above, all of these methods have problems, and therefore require further improvements. They are not considered to be effective methods for industrially preparing HFO-1234yf.

CITATION LIST

Patent Literature

PLT 1: WO2008/054781
PLT 2: WO2007/079431
PLT 3: US2009/0240090
PLT 4: WO2009/158321

SUMMARY OF INVENTION

Technical Problem

The present invention is completed in view of the current situation of the above-described conventional techniques. A main object of the present invention is to provide a process for efficiently preparing 2,3,3,3-tetrafluoropropene (HFO-1234yf) by a simple and economically advantageous method that is suitable for implementation on an industrial scale.

Solution to Problem

The present inventors conducted extensive studies to achieve the above object and, as a result, surprisingly found that the desired HFO-1234yf can be prepared with a high yield through the operation of a single-step reaction by a method in which 1,1,1,2,3-pentachloropropane (HCC-240 db) is used as a starting material and reacted with hydrogen fluoride (HF) in the gas phase under heating in the presence of oxygen, in the presence of a specific chromic oxide catalyst. Further, the present inventors found that it is possible to efficiently prepare HFO-1234yf on an industrial scale by eliminating problems in conventional HFO-1234yf preparation methods, and completed the present invention. In the present invention, the term "chromic oxide catalyst" may refer to chromic oxide or fluorinated chromic oxide obtained by fluorinating chromic oxide.

Additionally, stabilizers, such as polymerization inhibitors, are not required in the present invention because of the use of 1,1,1,2,3-pentachloropropane (HCC-240 db) as a starting material. Further, among products at the reactor outlet, at least one of the compounds (usable materials) represented by the structural formula: $CF_3R$ (a compound (HCFC-1233xf) wherein R is $-CCl=CH_2$, and a compound (HFC-245cb) wherein R is $-CF_2CH_3$) and hydrogen fluoride (HF) are recycled in a reactor. This makes it possible to efficiently prepare HFO-1234yf by a simple method.

Specifically, the present invention provides the following processes for preparing 2,3,3,3-tetrafluoropropene.

1. A process for preparing 2,3,3,3-tetrafluoropropene, comprising the step of:
    (1) in a reactor,
    (1-1) reacting 1,1,1,2,3-pentachloropropane with hydrogen fluoride in an amount of 10 to 100 mol per mole of the 1,1,1,2,3-pentachloropropane;
    (1-2) in the presence of chromic oxide represented by the composition formula: $CrO_m$ (1.5<m<3) or fluorinated chromic oxide obtained by fluorinating the chromic oxide;
    (1-3) in the presence of oxygen in an amount of 0.02 to 1 mol per mole of the 1,1,1,2,3-pentachloropropane; and (1-4) in the gas phase within a temperature range of 320 to 390° C., thereby obtaining a reaction product containing 2,3,3,3-tetrafluoropropene.

2. The preparation process according to Item 1, wherein the reaction product obtained in step (1) contains hydrogen chloride, 2,3,3,3-tetrafluoropropene, at least one compound selected from 2-chloro-3,3,3-trifluoropropene and 1,1,1,2,2-pentafluoropropane, and hydrogen fluoride; and the preparation process further comprises the step of: (2) recycling at least one compound selected from 2-chloro-3,3,3-trifluoropropene and 1,1,1,2,2-pentafluoropropane in the reaction product and hydrogen fluoride in the reactor.

3. The process according to Item 1 or 2, wherein the amount of the hydrogen fluoride is 15 to 50 mol per mole of the 1,1,1,2,3-pentachloropropane.

4. The process according to any one of Items 1 to 3, wherein the reaction pressure of the reactor is 0.08 to 0.8 MPa.

5. The process according to any one of Items 2 to 4, wherein step (1) and step (2) are continuously performed.

The process of the present invention for preparing 2,3,3,3-tetrafluoropropene is specifically described below.

(1) Starting Compound

In the present invention, 1,1,1,2,3-pentachloropropane (HCC-240 db) is used as a starting compound. The desired 2,3,3,3-tetrafluoropropene (HFO-1234yf) can be prepared with a high yield by a single-step reaction process by using the above compound as a raw material to react with hydrogen fluoride (HF) in accordance with the later-described conditions. 1,1,1,2,3-Pentachloropropane (HCC-240 db) is an advantageous starting compound in terms of easy availability and low cost.

(2) Reaction Method

The preparation process of the present invention is a process in which, in a rector, the 1,1,1,2,3-pentachloropropane (HCC-240 db) is reacted with hydrogen fluoride in the gas phase under heating in the presence of oxygen, in the presence of a specific chromic oxide catalyst. Specifically, the process of the present invention for preparing 2,3,3,3-tetrafluoropropene is characterized by comprising the step of:

(1) in a reactor, (1-1) reacting 1,1,1,2,3-pentachloropropane with hydrogen fluoride in an amount of 10 to 100 mol per mole of the 1,1,1,2,3-pentachloropropane;

(1-2) in the presence of chromic oxide represented by composition formula: $CrO_m$ ($1.5<m<3$) or fluorinated chromic oxide obtained by fluorinating the chromic oxide;

(1-3) in the presence of oxygen in an amount of 0.02 to 1 mol per mole of the 1,1,1,2,3-pentachloropropane; and (1-4) in the gas phase within a temperature range of 320 to 390° C., thereby obtaining a reaction product containing 2,3,3,3-tetrafluoropropene.

The desired 2,3,3,3-tetrafluoropropene (HFO-1234yf) can be obtained with high selectivity by a single-step reaction process, by reacting the starting compound with hydrogen fluoride under such conditions.

In the preparation process of the present invention, it is important that the above-described starting compound be reacted with hydrogen fluoride in the gas phase. The shape of the reactor used in the process of the present invention is not particularly limited. For example, an adiabatic reactor packed with a catalyst, a multitubular reactor in which a heating medium is used to remove heat and homogenize the temperature distribution in the reactor, and other like reactors may be used. In regard to the material of the reactor, a reactor formed of a material that is resistant to the corrosive action of hydrogen fluoride, such as Hastelloy, Inconel, Monel, and Incoloy, is preferably used.

Hydrogen fluoride (HF) may usually be supplied in the gas phase to a reactor together with a starting compound. The amount of hydrogen fluoride supplied is in the range of 10 to 100 mol, preferably about 15 to 50 mol, and more preferably about 15 to 35 mol, per mole of the above-described 1,1,1,2,3-pentachloropropane (starting compound, HCC-240 db). The formation of impurities can be reduced by setting the amount of hydrogen fluoride supplied within the above range, making it possible to recover HFO-1234yf from the product with high selectivity and a high yield.

Oxygen is usually supplied in an amount of 0.02 to 1 mol per mole of 1,1,1,2,3-pentachloropropane (HCC-240 db) as a starting compound. Oxygen is preferably supplied in the range of about 0.05 to 0.5 mol, and more preferably about 0.05 to 0.4 mol, per mole of HCC-240 db. The amount of oxygen supplied is set within the above range, thereby making it possible to prevent catalyst deterioration and maintain high catalytic activity. As for the form of oxygen supply, oxygen may be singly supplied, or oxygen may be diluted with an inert gas, such as nitrogen (which may be supplied as air), helium, argon, or the like.

Further, the reaction temperature (i.e., the temperature in the reactor) is in the range of 320 to 390° C., and more preferably about 330 to 380° C. These are temperature ranges in which the reaction is carried out in the gas phase. When the temperature is higher than the above temperature ranges, the selectivity of HFO-1234yf is decreased; while when the temperature is lower than the above temperature ranges, the period during which good catalytic activity can be maintained is shortened. Therefore, neither case is preferable.

Under the above-described reaction conditions and in the presence of a specific chromic oxide catalyst (described later), it is possible to obtain a reaction product containing $CF_3CF=CH_2$ (2,3,3,3-tetrafluoropropene, HFO-1234yf) at the reactor outlet, and $CF_3CF=CH_2$ (2,3,3,3-tetrafluoropropene, HFO-1234yf) can be separated and recovered from the reaction product.

In addition to $CF_3CF=CH_2$ (2,3,3,3-tetrafluoropropene, HFO-1234yf), the reaction product obtained in step (1) contains hydrogen chloride (HCl) formed from the starting compound, i.e., 1,1,1,2,3-pentachloropropane (HCC-240 db), and hydrogen fluoride (HF) that was supplied. Further, there is a case where the reaction product contains at least one compound selected from $CF_3CCl=CH_2$ (2-chloro-3,3,3-trifluoropropene, HCFC-1233xf) and $CF_3CF_2CH_3$ (1,1,1,2,2-pentafluoropropane, HFC-245cb).

In this case, after $CF_3CF=CH_2$ (2,3,3,3-tetrafluoropropene, HFO-1234yf) is separated and recovered from these components and hydrogen chloride (HCl) is removed, at least one compound (usable material) selected from $CF_3CCl=CH_2$ (2-chloro-3,3,3-trifluoropropene, HCFC-1233xf) and $CF_3CF_2CH_3$ (1,1,1,2,2-pentafluoropropane, HFC-245cb) and hydrogen fluoride (HF) are preferably recycled in the reactor used in step (1) (step (2)). By further performing this recycling operation, it is possible to prepare HFO-1234yf with a high yield.

When the usable material is recycled (step (2)), conditions such as the amounts of the hydrogen fluoride and oxygen supplied, the type of catalyst used, such as chromic oxide, and the reaction temperature are preferably as described in step (1).

It is also possible to prepare 2,3,3,3-tetrafluoropropene from at least one compound (usable material) selected from 2-chloro-3,3,3-trifluoropropene and 1,1,1,2,2-pentafluoropropane, by supplying the usable material to a different reactor.

As for the pressure during the reaction in the reactor, the reaction can be carried out at the above-described pressure at which 1,1,1,2,3-pentachloropropane (HCC-240 db) and hydrogen fluoride can exist in the gas phase, and the reaction may be carried out at a normal, increased, or reduced pressure, preferably within the range of 0.08 to 0.8 Mpa.

Although the reaction time is not particularly limited, the contact time represented by W/Fo, i.e., a ratio of the amount of packed catalyst W(g) to the total flow rate Fo (a flow rate at 0° C., 1 atm: cc/sec) of the raw material gases supplied to the reactor, may be generally adjusted to a range of 2 to 30 g·sec/cc, and preferably about 4 to 20 g·sec/cc. By setting the reaction time (W/Fo) within the above range, it is possible to maintain a high selectivity of HFO-1234yf.

The above-described pressure during reaction and reaction time in the reactor can be applied to both steps (1) and (2).

Further, in the preparation process of the present invention, HFO-1234yf can be prepared with a better yield by performing steps (1) and (2) in a continuous manner. For example, steps (1) and (2) can be performed as a continuous operation by the following manner: (i) the reaction of step (1) is performed; (ii) HCl is separated and removed from the reactor outlet components; (iii) HFO-1234yf is then separated; and subsequently, (iv) at least one compound of HFC-245cb and HCFC-1233xf, and HF are recycled.

In this way, an excellent preparation method of HFO-1234yf can be achieved under the reaction conditions in the ranges described above and by the use of a catalyst described below. HFO-1234yf obtained by separation and recovery can be recovered after HFO-1234yf is purified by distillation or the like to remove impurities formed by reaction, and may be used as-is in the intended application or converted to a different compound.

The concept of the present invention for preparing HFO-1234yf from HCC-240 db is shown in the following scheme.

the specific surface area is higher. The specific surface area when fluorinated is preferably about 25 to 130 $m^2/g$ and more preferably about 40 to 100 $m^2/g$; however, it is not limited to this range.

The fluorination reaction of chromic oxide may be performed prior to the implementation of the process of the present invention (described later) by supplying hydrogen fluoride to a reactor packed with chromic oxide. After chromic oxide is fluorinated by this method, the formation reaction of $CF_3CF=CH_2$(HFO-1234yf) can be progressed by supplying 1,1,1,2,3-pentachloropropane (HCC-240 db) as a raw material to the reactor.

The degree of fluorination is not particularly limited. For example, chromic oxide containing about 10 to 30% fluorine can be suitably used.

Further, the present invention can also use, as a chromium oxide catalyst or fluorinated chrome oxide catalyst, the amorphous chromium-based catalyst disclosed in Japanese Unexamined Patent Publication No. H11-171806, mainly comprising a chromium compound containing at least one metallic element selected from the group consisting of indium, gallium, cobalt, nickel, zinc, and aluminum, wherein chromium in the chromium compound has an average valence number of +3.5 or higher and +5.0 or less.

The above-described fluorination catalyst comprising chromic oxide or fluorinated chromic oxide may be used as supported on a carrier, such as alumina or activated carbon.

Because the present invention uses fluorination-treated chromic oxide for reaction, the use of fluorinated chromic oxide is particularly preferable.

Advantageous Effects of Invention

According to the present invention, 2,3,3,3-tetrafluoropropene (HFO-1234yf) can be prepared in a relatively short

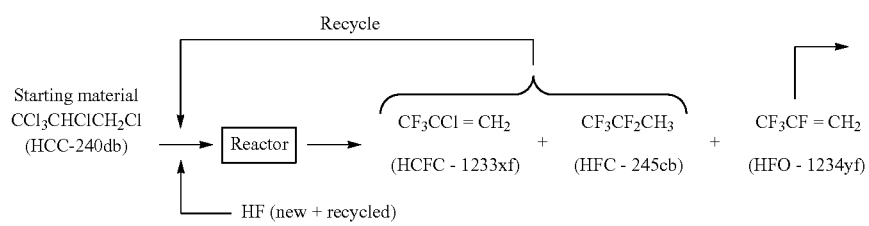

Among specific catalysts used in the present invention, an example of usable chromic oxide is one represented by the composition formula: CrOm, wherein m is in the range of 1.5<m<3, preferably 2≤m≤2.75, and more preferably 2≤m≤2.3. The form of chromic oxide catalyst is not limited. As long as the form is suitable for reaction, chromic oxide catalyst in any form, such as a powder or pellet, can be used, with a pellet being particularly preferable.

The above-described chromic oxide catalyst can be prepared, for example, by the method disclosed in Japanese Unexamined Patent Publication No. H05-146680. Further, fluorinated chromic oxide can also be prepared by the method disclosed in Japanese Unexamined Patent Publication No. H05-146680. For example, chromic oxide obtained by the above-described method is fluorinated (HF treatment) with hydrogen fluoride, thereby obtaining fluorinated chromic oxide. The temperature for fluorination is, for example, about 100 to 460° C.

The surface area of the catalyst is decreased by fluorination treatment. Generally, the catalyst becomes more active when contact time with high selectivity and a high yield by the operation of a single-step reaction using 1,1,1,2,3-pentachloropropane (HCC-240 db) as a raw material. Further, according to the process of the present invention, HFO-1234yf can be obtained with a high yield, and usable materials, such as $CF_3CCl=CH_2$ (HCFC-1233xf) and $CF_3CF_2CH_3$ (HFC-245cb), which are compounds other than HFO-1234yf and are precursors of HFO-1234yf, can also be obtained with high selectivity and a high yield. Further, usable materials, such as $CF_3CCl=CH_2$ (HCFC-1233xf) and $CF_3CF_2CH_3$ (HFC-245cb), can be recycled so as to be used as raw materials of HFO-1234yf.

Additionally, the preparation process of the present invention can be performed under mild conditions, such as normal pressure, reduced pressure, and the like. It is a preparation process that utilizes the gas phase, which is suitable for continuous production.

Further, according to the process of the present invention, the desired 2,3,3,3-tetrafluoropropene can be obtained while maintaining the long life of a catalyst, by eliminating drawbacks of conventional production methods that use catalysts.

Therefore, the process of the present invention is industrially very useful as a process for preparing 2,3,3,3-tetrafluoropropene (HFO-1234yf).

DESCRIPTION OF EMBODIMENTS

The present invention is described in further detail below with reference to preparation examples of 1,1,1,2,3-pentachloropropane (HCC-240 db) as a raw material and examples of the present invention.

Preparation Example 1

The following steps (1) to (3) are sequentially performed, thereby preparing 1,1,1,2,3-pentachloropropane (HCC-240 db).

(1) 1,1,1,3-Tetrachloropropane (HCC-250fb) Preparation Step

Soft iron powder (9.72 g, 171 mmol), triethyl phosphate (48 g, 260 mmol), ferric chloride (200 mg), and carbon tetrachloride (810 g, 5.26 mol) were placed in an autoclave (1,000 mL) equipped with a thermometer, a vacuum line, a nitrogen purge line, a feeding line, a gauge, and a pressure-opening valve. The mixture was purged with nitrogen 5 times and with ethylene 1 time. The inside of the autoclave was evacuated and ethylene was fed until the gauge pressure was 0.4 MPa while stirring. The reaction started when the autoclave was heated to 110° C. The inner temperature was raised to 134° C., and the pressured was dropped from 0.8 MPa to 0.25 MPa. While maintaining the ethylene pressure at 0.8 MPa, the mixture was stirred at an inner temperature of 120° C. for 9 hours. Subsequently, triethyl phosphate (24 g, 130 mmol) was injected, and the reaction was further carried out at 120° C. for 7 hours.

After the reaction was completed, the crude product was analyzed by gas chromatography, and a complete consumption of carbon tetrachloride was confirmed. The crude product was washed twice with water in an amount three times the volume of the crude product, and the organic layer was dried on magnesium sulfate, thereby obtaining HCC-250fb having a gas chromatography purity of 79.8%. A by-product was an oligomer in which HCl is bound to ethylene.

The thus-obtained crude product was distilled under reduced pressure (10 mmHg) to collect fractions of 70 to 74° C., thereby obtaining HCC-250fb (814 g, 4.94 mol, yield of 91%) having a purity of 98% or higher.

(2) 1,1,3-Trichloropropene (HCC-1240za) and 3,3,3-Trichloropropene (HCC-1240zf) Preparation Step HCC-250fb (540 g, 3.0 mol) obtained in step (1), 40% KOH aqueous solution (630 g), and a phase transfer catalyst (Aliquat 336, 10 g) were placed in a four-necked flask (1,000 mL) equipped with a thermometer and a cooling tube. While stirring, the mixture was reacted in an oil bath at 80° C. for 3 hours. After the reaction was completed, the reaction product was cooled and distilled under reduced pressure (10 to 20 mmHg) to collect fractions of 67.7 to 81.9° C., thereby obtaining a mixture (390 g, 2.68 mol, yield of 89.3%) having a ratio of HCC-1240zf:HCC-1240za=62:38.

(3) 1,1,1,2,3-Pentachloropropane (HCC-240 db) Preparation Step

The mixture (265 g) of 1,1,3-trichloropropene (HCC-1240za) and 3,3,3-trichloropropene (HCC-1240zf), which was obtained in step (2), was placed in a flask (500 mL) equipped with a high-pressure mercury vapor lamp, a magnetic stirrer, and two gas inlets, followed by cooling to 0° C. in an ice bath. The content was stirred while being irradiated with ultraviolet light, and chlorine gas was introduced at 20 to 120 mL/min from one gas inlet to the space above the liquid surface of the content. The reaction mixture was occasionally sampled to analyze the reaction mixture by gas chromatography analysis so as to measure the degree of chlorination. Three hours later, all trichloropropenes were consumed, and 370 g of a product was obtained. The thus-obtained product was distilled under reduced pressure (3 mmHg) to collect fractions of 51 to 53° C., thereby obtaining 1,1,1,2,3-pentachloropropane (HCC-240 db) (330 g) with a purity of 99.6%.

Example 1

17.2 g of a catalyst (containing about 17.0% of fluorine) obtained by fluorinating chromic oxide comprising a composition of $CrO_{2.0}$ was packed in a tubular reactor made of Hastelloy having an inner diameter of 15 mm and a length of 1 m. In the inside of the reactor, insertion tubes were inserted from the top to measure the temperature in the inside of the catalytic packed-bed reactor at three points, and the average of these temperatures was regarded as the reaction temperature.

The inside of the reactor was maintained at atmospheric pressure (1 atm) and 300° C., and 160 cc/min of anhydrous hydrogen fluoride (HF) (flow rate at 0° C., 1 atm) and 100 cc/min of nitrogen ($N_2$) (flow rate at 0° C., 1 atm) were supplied to the reactor for 2 hours. Subsequently, the supply of nitrogen ($N_2$) was stopped, the reactor temperature was changed to 360° C., and oxygen ($O_2$) was supplied to the reactor at 2.0 cc/min (flow rate at 0° C., 1 atm) for an additional 1 hour. Then, 1,1,1,2,3-pentachloropropane (HCC-240 db, purity of 99.6%) was supplied at a rate of 10.0 cc/min (flow rate at 0° C., 1 atm), and the reaction was started at this point. The molar ratio of HF to 1,1,1,2,3-pentachloropropane (HCC-240 db) was 16, and the contact time ($W/F_0$) was 6.0 g·sec/cc.

Of the reaction products, high-boiling-point products having a boiling point of 50° C. or higher were quantified in the manner described below. Specifically, HCFC-225 in which a predetermined amount of perchloroethylene was dissolved as an internal standard material was mixed with ice water to achieve liquid separation. Reactor outlet components were bubbled into the HCFC-225 layer for a certain period of time so as to extract organic materials from the HCFC-225 layer, and the acid content in hydrogen fluoride and hydrogen chloride was dissolved in the ice water.

The extract was heated to 20° C., and the HCFC-225 layer was analyzed by gas chromatography (FID) using a DB-624 (60 m) capillary column as the column. The production amount of each product was converted to a molar ratio based on the ratio of the detected area of perchloroethylene as the internal standard material to the detected area of each product, by considering the coefficient of each product in gas chromatography.

On the other hand, low-boiling-point products having a boiling point of 50° C. or lower were quantified in the manner described below. Specifically, two washing columns that were connected in series and filled with water were coupled to the reactor outlet and immersed in a water bath to, be preliminarily heated to 60° C. Subsequently, the reactor effluent was introduced into the washing columns and subjected to bubbling to wash the acid content. Then, the gas component dehydrated through a CaCl$_2$ tube was collected and analyzed by gas chromatography (FID). At this time, a predetermined amount of HFC-32 as the internal standard material was introduced together with the reactor effluent from the reactor outlet side to the washing columns. A GS-GasPro (60 m) capillary column was used as the column. The production amount of each product was converted to a molar ratio based on the ratio of the detected area of HFC-32 as the internal standard material to the detected area of each product, by considering the coefficient of each product in gas chromatography.

Using the above method, the reactor outlet components were quantified along with the passage of time from the start of the reaction. Table 1 shows the results obtained at 22 hours and 165 hours after the start of the reaction as Examples 1-1 and 1-2, respectively.

Products obtained in this Example are as follows. Of the four compounds below, all of the compounds except for the desired compound (i.e., HFO-1234yf) are precursors of HFO-1234yf and are considered to be usable materials because they can be recycled and used as raw materials.

CF$_3$CF=CH$_2$ (HFO-1234yf)
CF$_3$CCl=CH$_2$ (HCFC-1233xf)
CF$_3$CF$_2$CH$_3$ (HFC-245cb)

The following compounds are regarded as impurities formed in this reaction.

CF$_3$CCl=CHCl (HCFC-1223xd-E form+Z form)
CF$_3$CH=CHCl (HCFC-1233zd-E form+Z form)
CF$_3$CH=CHF (HFC-1234ze-E form+Z form)
CF$_3$CH$_2$CHF$_2$ (HFC-245fa)
CF$_3$CH=CH$_2$ (HFC-1243zf)

Example 2

A reaction was carried out under conditions similar to those of Example 1, except that the amount of packed catalyst used was changed to 39.0 g; anhydrous hydrogen fluoride (HF) was supplied to the reactor at 224 cc/min (flow rate at 0° C., 1 atm); oxygen (O$_2$) was supplied to the reactor at 0.8 cc/min (flow rate at 0° C., 1 atm); 1,1,1,2,3-pentachloropropane (HCC-240 db, purity of 99.6%) was supplied to the reactor at 8.0 cc/min (flow rate at 0° C., 1 atm); and the reaction temperature was changed to 355° C. The molar ratio of HF to 1,1,1,2,3-pentachloropropane (HCC-240 db) was 28, and the contact time (W/F$_0$) was 10.1 g·sec/cc. Table 1 shows the results of analysis at a time point 39 hours after the start of the reaction.

Example 3

A reaction was carried out under conditions similar to those of Example 1, except that the amount of packed catalyst used was changed to 34.0 g; anhydrous hydrogen fluoride (HF) was supplied to the reactor at 192 cc/min (flow rate at 0° C., 1 atm); 1,1,1,2,3-pentachloropropane (HCC-240 db, purity 99.6%) was supplied to the reactor at 8.0 cc/min (flow rate at 0° C., 1 atm); and the reaction temperature was changed to 345° C. The molar ratio of HF to 1,1,1,2,3-pentachloropropane (HCC-240 db) was 24, and the contact time (W/F$_0$) was 10.1 g·sec/cc. Table 1 shows the results of analysis at a time point 28 hours after the start of the reaction.

Comparative Examples are shown below to compare the characteristics of the present invention.

Comparative Example 1

A reaction was carried out under conditions similar to those of Example 1, except that oxygen (O$_2$) was supplied to the reactor at 4.0 cc/min (flow rate at 0° C., 1 atm) and the reaction temperature was changed to 305° C. The molar ratio (WIT to 1,1,1,2,3-pentachloropropane (HCC-240 db) was 16, and the contact time (W/F$_0$) was 5.9 g·sec/cc. Table 2 shows the results obtained 166 hours after the start of the reaction as Comparative Example 1.

In addition to the products described in Examples, compounds that serve as intermediates were formed in this Comparative Example. These compounds are as follows:

CCl$_2$=CClCH$_2$Cl (HCC-1230xa)
CF$_2$ClCCl=CH$_2$ (HCFC-1232xf)
CFCl$_2$CCl=CH$_2$ (HCFC-1231xf)
CF$_2$ClCHClCH$_2$Cl (HCFC-242dc)
CFCl$_2$CHClCH$_2$Cl (HCFC-241 db)

Comparative Example 2

A reaction was carried out under conditions similar to those of Example 1, except that the temperature was changed to 405° C. The molar ratio of HF to 1,1,1,2,3-pentachloropropane (HCC-240 db) was 16, and the contact time (W/F$_0$) was 6.0 g·sec/cc. Table 2 shows the results obtained 12 hours after the start of the reaction as Comparative Example 2.

Comparative Example 3

A reaction was carried out under conditions similar to those of Example 1, except that no oxygen (O$_2$) was supplied to the reactor and the temperature was changed to 355° C. The molar ratio of HF to 1,1,1,2,3-pentachloropropane (HCC-240 db) was 16, and the contact time (W/F$_0$) was 6.1 g·sec/cc. Table 2 shows the results obtained 24 and 190 hours after the start of the reaction as Comparative Examples 3-1 and 3-2, respectively.

Comparative Example 4

A reaction was carried out under conditions similar to those of Example 1, except that the amount of packed catalyst used was changed to 15.2 g; anhydrous hydrogen fluoride (HF) was supplied to the reactor at 80 cc/min (flow rate at 0° C., 1 atm); oxygen (O$_2$) was supplied to the reactor at 1.0 cc/min (flow rate at 0° C., 1 atm); and the reaction temperature was changed to 355° C. The molar ratio of HF to 1,1,1,2,3-pentachloropropane (HCC-240 db) was 8, and the contact time (W/F$_0$) was 10.0 g·sec/cc. Table 2 shows the results at a time point 16 hours after the start of the reaction as Comparative Example 4.

TABLE 1

|  | Example 1-1 | Example 1-2 | Example 2 | Example 3 |
|---|---|---|---|---|
| Reaction temperature (° C.) | 360 | 360 | 355 | 345 |
| Molar ratio (HF/240 db) | 16 | 16 | 28 | 24 |
| W/F$_0$ (g · sec./cc) | 6.0 | 6.0 | 10.1 | 10.1 |
| O$_2$/240 db (mol %) | 20 | 20 | 10 | 25 |

TABLE 1-continued

|  | Example 1-1 | Example 1-2 | Example 2 | Example 3 |
|---|---|---|---|---|
| Time (h) after the start of the reaction | 22 | 165 | 39 | 28 |
| Conversion (%) of raw material | 100 | 100 | 100 | 100 |
| Selectivity (%) of useful materials |  |  |  |  |
| HFO-1234yf | 13.6 | 13.7 | 16.3 | 12.5 |
| HCFC-1233xf | 79.9 | 79.6 | 77.2 | 82.6 |
| HFC-245cd | 2.4 | 2.5 | 4.3 | 3.4 |
| Selectivity (%) of impurities |  |  |  |  |
| HCFC-1223xd | 2.1 | 2.1 | 1.0 | 0.7 |
| HCFC-1233zd | 0.3 | 0.3 | 0.2 | 0.1 |
| HFO-1234ze | 0.2 | 0.2 | 0.1 | 0.1 |
| HFC-245fa | 0.1 | 0.1 | 0.1 | 0 |
| HFC-1243zf | 0.2 | 0.2 | 0.1 | 0.1 |
| Others | 1.2 | 1.3 | 0.7 | 0.5 |

In the table, "Molar ratio (HF/240 db)" indicates the molar ratio of HF to 1,1,1,2,3-pentachloropropane (HCC-240 db). For example, the table shows that 16 mol of HF is supplied per mole of 240 db in Example 1-1.

In the table, "$O_2$/240 db (mol %)" indicates the ratio of $O_2$ to 1,1,1,2,3-pentachloropropane (HCC-240 db) in mol %. For example, the table shows that 20 mol of $O_2$ is supplied relative to 100 mol of 240 db (in other words, 0.2 mol of $O_2$ is supplied per mole of 240 db) in Example 1-1.

In Comparative Example 4, the amount of HF supplied per mole of HCC-240 db was less than 10 mol, and the selectivity of impurities was high. Consequently, the selectivity of HFO-1234yf was low.

In contrast, in the Examples, HFO-1234yf was obtained using HCC-240 db as a starting material by a method in which HCC-240 db is reacted with a specific amount of HF under heating in the presence of a specific amount of oxygen relative to HCC-240 db, in the presence of a specific chromic

TABLE 2

|  | Comparative Example 1 | Comparative Example 2 | Comparative Example 3-1 | Comparative Example 3-2 | Comparative Example 4 |
|---|---|---|---|---|---|
| Reaction temperature (° C.) | 305 | 405 | 355 | 355 | 355 |
| Molar ratio (HF/240 db) | 16 | 16 | 16 | 16 | 8 |
| W/F$_0$ (g · sec./cc) | 5.9 | 6.0 | 6.1 | 6.1 | 10.0 |
| O$_2$/240 db (mol %) | 40 | 20 | 0 | 0 | 10 |
| Time (h) after the start of the reaction | 166 | 12 | 24 | 190 | 16 |
| Conversion (%) of raw material | 93.2 | 100 | 99.6 | 83.5 | 100 |
| Selectivity (%) of useful materials |  |  |  |  |  |
| HFO-1234yf | 0.2 | 17.2 | 1.6 | 0.2 | 14.2 |
| HCFC-1233xf | 88.2 | 66.8 | 93.5 | 81.0 | 71.7 |
| HFC-245cd | 0.1 | 1.9 | 0.4 | 0.1 | 2.8 |
| Selectivity (%) of other intermediates |  |  |  |  |  |
| HCC-1230xa | 3.0 | 0 | 1.2 | 7.9 | 1.6 |
| HCFC-1232xf | 1.8 | 0 | 0.5 | 5.5 | 0.9 |
| HCFC-1231xf | 0.4 | 0 | 0 | 1.0 | 0.2 |
| HCFC-242dc | 0.5 | 0 | 0 | 0.4 | 0.6 |
| HCFC-241db | 0.3 | 0 | 0.1 | 1.8 | 0 |
| Selectivity (%) of impurities |  |  |  |  |  |
| HCFC-1223xd | 1.9 | 4.3 | 0.4 | 0.3 | 2.1 |
| HCFC-1233zd | 0.4 | 1.3 | 0.3 | 0.3 | 1.4 |
| HFO-1234ze | 0.1 | 0.6 | 0.2 | 0.2 | 0.5 |
| HFC-245fa | 0 | 0.2 | 0 | 0 | 0.2 |
| HFC-1243zf | 0.1 | 0.6 | 0.2 | 0.2 | 0.4 |
| Others | 3.0 | 7.1 | 1.6 | 1.1 | 3.4 |

In Comparative Example 1, the reaction temperature was less than 320° C., and the catalytic activity could not be sufficiently maintained. Therefore, the selectivity of HFO-1234yf was low.

Further, in Comparative Example 2, the reaction temperature exceeded 390° C. The selectivity of the usable materials was low, and the selectivity of impurities was high.

In Comparative Examples 3-1 and 3-2, the reaction was carried out without an oxygen supply, and the catalytic activity was decreased in a short period of time. Therefore, the selectivity of HFO-1234yf was low.

oxide catalyst. HFO-1234yf was prepared with high selectivity and a high yield. Further, in the Examples, usable materials such as $CF_3CCl=CH_2$ (HCFC-1233xf) and $CF_3CF_2CH_3$ (HFC-245cb), i.e., compounds other than HFO-1234yf and precursors of HFO-1234yf, were also obtained with high selectivity and a high yield. These usable materials were able to be recycled and used as raw materials.

The invention claimed is:

1. A process for preparing 2,3,3,3-tetrafluoropropene, comprising the step of:

(1) in a reactor,
- (1-1) reacting 1,1,1,2,3-pentachloropropane with hydrogen fluoride in an amount of 10 to 100 mol per mole of the 1,1,1,2,3-pentachloropropane;
- (1-2) in the presence of chromic oxide represented by composition formula: $CrO_m$ ($1.5<m<3$) or fluorinated chromic oxide obtained by fluorinating the chromic oxide;
- (1-3) in the presence of oxygen in an amount of 0.02 to 1 mol per mole of the 1,1,1,2,3-pentachloropropane; and
- (1-4) in the gas phase within a temperature range of 320 to 390° C., thereby obtaining a reaction product containing 2,3,3,3-tetrafluoropropene.

2. The preparation process according to claim 1, wherein the reaction product obtained in step (1) contains hydrogen chloride, 2,3,3,3-tetrafluoropropene, at least one compound selected from 2-chloro-3,3,3-trifluoropropene and 1,1,1,2,2-pentafluoropropane, and hydrogen fluoride; and the preparation process further comprises the step of:
(2) recycling at least one compound selected from 2-chloro-3,3,3-trifluoropropene and 1,1,1,2,2-pentafluoropropane in the reaction product and hydrogen fluoride in the reactor.

3. The process according to claim 1, wherein the amount of the hydrogen fluoride is 15 to 50 mol per mole of the 1,1,1,2,3-pentachloropropane.

4. The process according to claim 1, wherein the reaction pressure of the reactor is 0.08 to 0.8 MPa.

5. The process according to claim 2, wherein step (1) and step (2) are continuously performed.

6. The process according to claim 2, wherein the amount of the hydrogen fluoride is 15 to 50 mol per mole of the 1,1,1,2,3-pentachloropropane.

7. The process according to claim 2, wherein the reaction pressure of the reactor is 0.08 to 0.8 MPa.

8. The process according to claim 3, wherein the reaction pressure of the reactor is 0.08 to 0.8 MPa.

9. The process according to claim 6, wherein the reaction pressure of the reactor is 0.08 to 0.8 MPa.

10. The process according to claim 3, wherein step (1) and step (2) are continuously performed.

11. The process according to claim 4, wherein step (1) and step (2) are continuously performed.

12. The process according to claim 6, wherein step (1) and step (2) are continuously performed.

13. The process according to claim 7, wherein step (1) and step (2) are continuously performed.

14. The process according to claim 8, wherein step (1) and step (2) are continuously performed.

15. The process according to claim 9, wherein step (1) and step (2) are continuously performed.

* * * * *